(12) United States Patent
Rappel

(10) Patent No.: US 9,919,070 B2
(45) Date of Patent: Mar. 20, 2018

(54) FRAGRANCE DISPENSER AND A HEATING, VENTILATION, AND AIR CONDITIONING SYSTEM HAVING SUCH A FRAGRANCE DISPENSER

(71) Applicant: MAHLE International GmbH, Stuttgart (DE)

(72) Inventor: Thomas Rappel, Stuttgart (DE)

(73) Assignee: MAHLE International GmbH, Stuttgart (DE)

( * ) Notice: Subject to any disclaimer, the term of this patent is extended or adjusted under 35 U.S.C. 154(b) by 71 days.

(21) Appl. No.: 15/239,898

(22) Filed: Aug. 18, 2016

(65) Prior Publication Data
US 2017/0065737 A1 Mar. 9, 2017

(30) Foreign Application Priority Data
Sep. 9, 2015 (DE) .......................... 10 2015 217 250

(51) Int. Cl.
*B01F 3/04* (2006.01)
*A61L 9/12* (2006.01)
*B60H 3/00* (2006.01)

(52) U.S. Cl.
CPC .............. *A61L 9/12* (2013.01); *B01F 3/0446* (2013.01); *B01F 3/04099* (2013.01); *B60H 3/0007* (2013.01); *A61L 2209/133* (2013.01); *A61L 2209/16* (2013.01)

(58) Field of Classification Search
CPC ...... B01F 3/04; B01F 3/04099; B01F 3/0446; A61L 9/12; A61L 9/122; B60H 3/0007
USPC ............................................ 261/30, DIG. 88
See application file for complete search history.

(56) References Cited

U.S. PATENT DOCUMENTS 3,298,674 A 1/1967 Gilbertson
8,931,712 B2* 1/2015 Nagano ..................... A61L 9/12
165/202

FOREIGN PATENT DOCUMENTS

| DE | 20 2005 015 709 U1 | 1/2006 |
| DE | 10 2007 010 796 A1 | 9/2008 |
| DE | 10 2010 008 436 A1 | 8/2011 |
| EP | 2 269 850 A1 | 1/2011 |
| WO | WO 2010/068074 A2 | 6/2010 |

* cited by examiner

*Primary Examiner* — Robert A Hopkins
(74) *Attorney, Agent, or Firm* — Muncy, Geissler, Olds & Lowe, P.C.

(57) ABSTRACT

A fragrance dispenser, in particular for a heating, ventilation, and air conditioning system, with a fragrance container with a connection opening and with a container cover with an air inlet channel and an air outlet channel, further, with a movable operating element, and a movable valve element by means of which the air inlet channel and the air outlet channel can be opened and closed, wherein the valve element can be actuated by the operating element, and wherein further a bypass channel can be controlled by the operating element.

24 Claims, 8 Drawing Sheets

FRAGRANCE DISPENSER AND A HEATING, VENTILATION, AND AIR CONDITIONING SYSTEM HAVING SUCH A FRAGRANCE DISPENSER

This nonprovisional application claims priority under 35 U.S.C. § 119(a) to German Patent Application No. 10 2015 217 250.3, which was filed in Germany on Sep. 9, 2015, and which is herein incorporated by reference.

BACKGROUND OF THE INVENTION

Field of the Invention

The invention relates to a fragrance dispenser. In addition, the invention relates to a heating, ventilation, and air conditioning system having such a fragrance dispenser.

Description of the Background Art

DE 20 2005 015 709 U1 discloses a fragrance device for climate control systems with a container filled with a scented liquid and an operating element partially immersed in the scented liquid, as well as a bypass line, conveying at least one part of a primary air flow from a main ventilation line to the operating element. In this case, a secondary air flow is established and the fragrance device has adjusting means for changing the operating element part acted upon by the secondary air flow.

DE 10 2007 010 796 A1 discloses an arrangement with a fragrance device, in particular for a motor vehicle, which has an air intake channel, an exhaust air channel, a fan, and a means for receiving a fragrance, whereby a temperature sensor is placed in the air intake channel or the exhaust air channel. In addition, DE 10 2007 010 796 A1 discloses a method for operating an arrangement of this kind.

EP 2 269 850 A1 discloses a fragrance system for a motor vehicle comprising a fragrance receiving unit for receiving a liquid fragrance, an air conveying device for conveying air through the fragrance receiving unit, in order to introduce the fragrance into a vehicle interior by means of the conveyed air, whereby the fragrance receiving unit has an inlet port for introducing the air, conveyed by the air conveying unit, into the fragrance receiving unit and a discharge opening for discharging the conveyed air out of the fragrance receiving unit. Moreover, the fragrance system has a first shut-off element for closing and opening the discharge opening, so that when a first shut-off element is open, fragrance can be introduced into the vehicle interior and when a first shut-off element is closed, no fragrance can be introduced into the vehicle interior.

SUMMARY OF THE INVENTION

It is therefore an object of the invention to provide a more improved fragrance dispenser. In addition, it is an object of the invention to provide a heating, ventilation, and air conditioning system with which such a fragrance dispenser can be used.

An exemplary embodiment of the invention relates to a fragrance dispenser, in particular for a heating, ventilation, and air conditioning system, with a fragrance container with a connection opening and with a container cover with an air inlet channel and an air outlet channel, further, with a movable operating element, and a movable valve element, by means of which the air inlet channel and the air outlet channel can be opened and closed, whereby the valve element can be actuated by the operating element, whereby further a bypass channel can be controlled by the operating element. A choice can be made in an advantageous manner in this case between supplying a vehicle cabin with a fragrance and ventilating the vehicle cabin with fragrance-free air.

An advantageous embodiment of the fragrance dispenser provides that the operating element and the valve element can be arranged axially one behind the other and axially slidable at least partially in a guide sleeve and the air inlet channel and the air outlet channel are arranged adjacent and parallel to the longitudinal axis of the guide sleeve. This allows an actuation option for the valve element that is structurally simple to implement.

In an exemplary embodiment of the fragrance dispenser, the bypass channel can have a first bypass channel element and a second bypass channel element, whereby the first bypass channel element is formed on the operating element and the second bypass channel element is formed on the guide sleeve.

An embodiment of the fragrance dispenser provides that the bypass channel can be opened or closed for fluid throughflow by means of an axial operating element movement, made relative to the guide sleeve. The basis for a control option that is structurally simple to implement for the bypass channel is created in this way.

In an exemplary embodiment of the fragrance dispenser, the first bypass channel element can have a circumferential first annular groove situated on the operating element and the second bypass channel element has at least one bypass inlet opening, arranged radially on the guide sleeve, and at least one bypass outlet opening, arranged radially on the guide sleeve. A cost-effective embodiment of the bypass channel that can be realized in a few fabrication steps is created in this way.

An embodiment of the fragrance dispenser provides that the first bypass element can have a channel passing through the operating element substantially perpendicular to the longitudinal axis of the operating element. This is a further bypass channel design form that is cost-effective and can be fabricated in a few production steps.

In an exemplary embodiment of the fragrance dispenser, the air inlet channel can have a first air inlet channel opening at a first air inlet channel end, pointing toward the fragrance container, and the air outlet channel has a first air outlet channel opening at the first air outlet channel end, pointing toward the fragrance container, and the valve element has a valve disc at a first valve element end, pointing toward the fragrance container, whereby by means of an axial movement of the valve element and the valve disc, the first air inlet channel opening and the first air outlet channel opening can be opened or closed for throughflow of a fluid. A simple and space-saving solution for augmenting a fluid stream with a fragrance is created in this way.

An embodiment of the fragrance dispenser provides that the valve element can be loaded by means of at least one first return spring in a first direction, pointing away from the fragrance container, toward a first operating element end, pointing toward the fragrance container.

In an embodiment of the fragrance dispenser, the at least one first return spring can be supported against a bridge element, whereby the bridge element is connected to a first container cover side, pointing toward the fragrance container. This allows the axial actuation of the valve element by means of an axial displacement of the operating element.

An embodiment of the fragrance dispenser provides that the operating element can be loaded by means of a second return spring in the first direction toward a first guide sleeve end.

In an embodiment of the fragrance dispenser, the second return spring can be supported against a counter support formed in the area of a second valve element end, pointing toward the operating element.

An embodiment of the fragrance dispenser provides that a circumferential projection can be formed at the first operating element end, whereby the circumferential projection can be supported against a shoulder formed in the area of a first guide sleeve end. In this regard, the guiding of the operating element is supported in a structurally simple manner.

In an embodiment of the fragrance dispenser, the container cover can have connectors by means of which the air inlet channel and/or the air outlet channel and/or the bypass inlet opening and/or the bypass outlet opening can be connected to a fluid channel arrangement and/or a duct arrangement of a heating, ventilation, and air conditioning system.

An exemplary embodiment of the fragrance dispenser provides that the fragrance container can have an edge pointing toward the container cover, whereby at least one radially arranged circumferential second annular groove is formed on the edge, whereby at least one first O-ring, which lies against a cover inner wall formed by the container cover in a radially inwardly sealing manner, is disposed in the area of the at least one second annular groove.

In an embodiment of the fragrance dispenser, the valve element in the area of the second valve element end can have at least one radially arranged circumferential third annular groove, whereby at least one second O-ring, which lies against a sleeve inner wall formed by the guide sleeve in a radially inwardly sealing manner, is disposed in the area of the at least one third annular groove.

An exemplary embodiment of the fragrance dispenser provides that the container cover can have at least one first connecting element and the fragrance container has at least one second connecting element corresponding to the first connecting element, whereby the container cover and the fragrance container can be connected together by means of the two connecting elements.

In an embodiment of the fragrance dispenser, the at least one first connecting element and the at least one second connecting element form a clip and/or plug connection. This allows a simple and cost-effective connection of the fragrance container to the container cover.

An exemplary embodiment of the fragrance dispenser provides that the container cover can have at least one first attachment element, which corresponds to a second attachment element disposed on a housing element of a heating, ventilation, and air conditioning system in such a way that the first attachment element and the second attachment element can be connected together.

In an embodiment of the fragrance dispenser, the first attachment element and the second attachment element can be connected to form a bayonet catch. This allows a simple and cost-effective connection of the fragrance dispenser to a heating, ventilation, and air conditioning system.

An exemplary embodiment of the fragrance dispenser provides that the container cover on a second container cover side, lying opposite to the first container cover side, can have a substantially centrally disposed attachment region, whereby the operating element and the guide sleeve are arranged centrally within the attachment region.

In an embodiment of the fragrance dispenser, the attachment region can have an inner tube connection and an outer tube connection, radially surrounding the inner tube connection, whereby the operating element and the guide sleeve are arranged centrally within the inner tube connection and perpendicular to a plane formed by the cross section of the inner tube connection.

An exemplary embodiment of the fragrance dispenser provides that the air inlet channel can have a second air inlet channel end, lying opposite to the first air inlet channel end, and the air outlet channel can have a second air outlet channel end, lying opposite to the first air outlet channel end, whereby the second air inlet channel end and the second air outlet channel end are arranged radially between the inner tube connection and the outer tube connection.

An exemplary embodiment of the heating, ventilation, and air conditioning system provides that at least one fragrance dispenser designed according to the description above is disposed in the heating, ventilation, and air conditioning system.

In an embodiment of the heating, ventilation, and air conditioning system, two fragrance dispensers can be disposed in the heating, ventilation, and air conditioning system.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
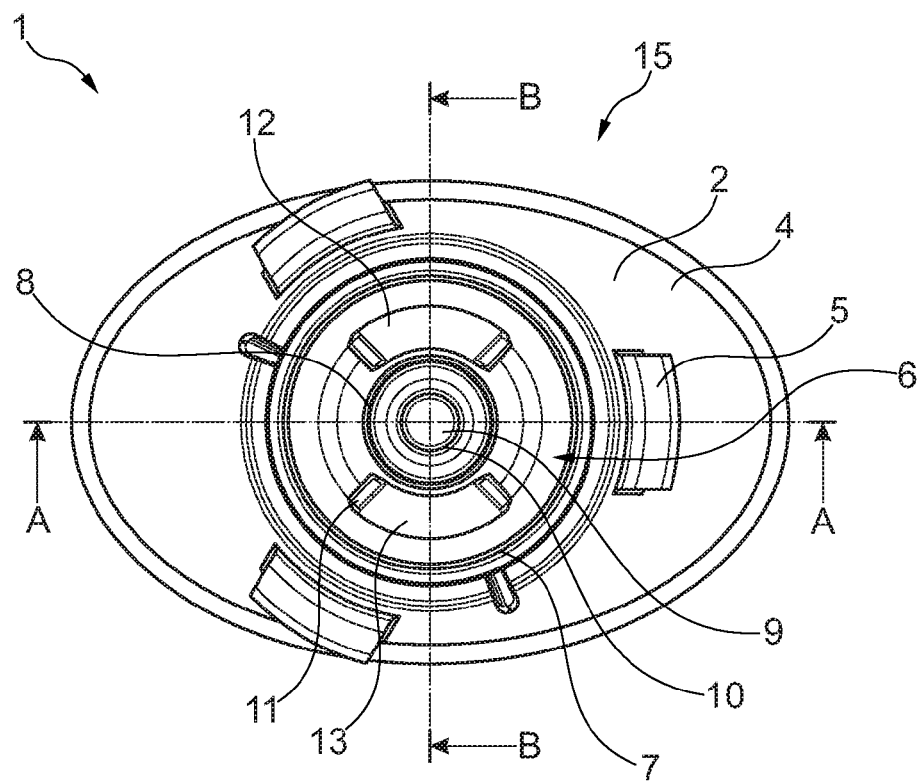
FIG. 1 shows a perspective top plan view of a fragrance dispenser.
Figure 2:
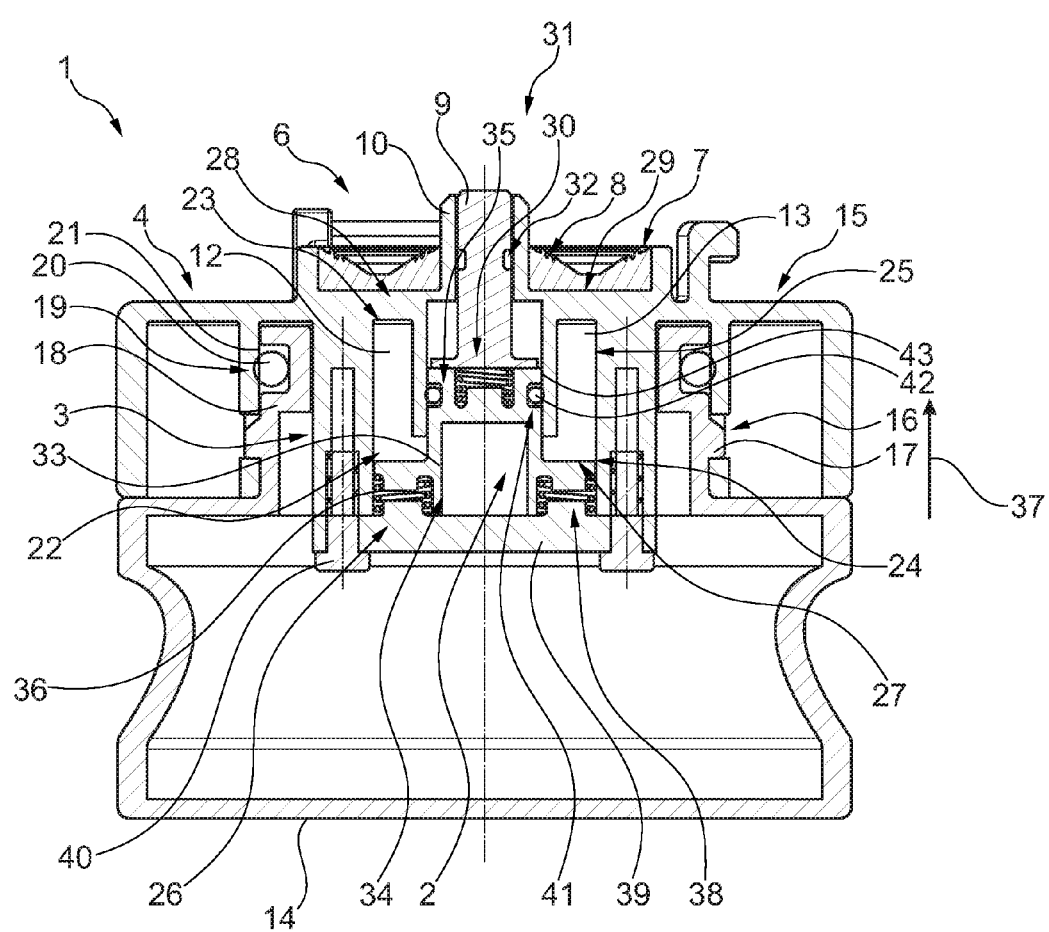
FIG. 2 shows a side sectional view of a fragrance dispenser according to FIG. 1.

A perspective top plan view of a fragrance dispenser 1 is shown in FIG. 1. A section line A-A, which results in the side sectional view shown in FIG. 2, is shown in the figure. Moreover, a section line B-B, which results in FIGS. 3, 4, 5, and 6, is shown in FIG. 1.

Fragrance dispenser 1 shown in FIG. 1 has a container cover 15 formed substantially oval in the top plan view. Container cover 15 has a first container cover side 3, which is not shown because of the viewing direction in FIG. 1, and a second container cover side 4.

Three first attachment elements 5 are formed on second container cover side 4. First attachment elements 5 are arranged in a substantially circular manner and in each case can be connected to a second attachment element (not shown), whereby the second attachment elements are arranged on a housing element of a heating, ventilation, and air conditioning system (not shown). In the exemplary embodiment shown in FIG. 1, first attachment elements 5 in each case are formed by way of example as part of a bayonet catch.

An attachment region 6 is located on second container cover side 4 radially within three first attachment elements 5, arranged substantially in a circle. Attachment region 6 has an outer tube connection 7 and an inner tube connection 8 arranged concentrically within outer tube connection 7. Fragrance dispenser 1 can be connected to a fluid channel arrangement (not shown) of the heating, ventilation, and air conditioning system by means of outer tube connection 7 and inner tube connection 8.

An operating element 9 is arranged radially within inner tube connection 8, centrally and perpendicular to a plane formed by the cross section of inner tube connection 8. Operating element 9 is arranged sliding axially in a guide sleeve 10.

Four partition walls 11, which separate an air inlet channel 12 and an air outlet channel 13 from one another, are shown between inner tube connection 8 and outer tube connection 7.

A side sectional view of fragrance dispenser 1 is shown in FIG. 2. Fragrance dispenser 1 has a fragrance container 14 with a connection opening 2 and a container cover 15 inserted in connection opening 2. Container cover 15 and fragrance container 14 are connected by means of a first connecting element 16 formed on container cover 15 and a second connecting element 17 formed on fragrance container 14 and corresponding to first connecting element 16. In the exemplary embodiment shown in FIG. 2, first connecting element 16 and second connecting element 17 by way of example form a clip connection.

A fragrance (not shown) can be located in fragrance container 14. Fragrance container 14 has an edge 18 pointing toward container cover 15. An annular groove 19 is formed in the area of edge 18. A first O-ring 20 is disposed in the area of annular groove 19. First O-ring 20 in this case lies sealingly on a cover inner wall 21 of container cover 15.

Container cover 15 has a first container cover side 3, pointing toward fragrance container 14, and a second container cover side 4, pointing away from the fragrance container. An attachment region 6 is located centrally in the area of second container cover side 4. Attachment region 6 has a round outer tube connection 7 and a round inner tube connection 8. An air inlet channel 12 and an air outlet channel 13 are disposed radially between inner tube connection 8 and outer tube connection 7 vertically to a plane formed by the cross section of tube connections 7 and 8.

Air inlet channel 12 has a first air inlet channel end 22, pointing toward fragrance container 14, and a second air inlet channel end 23, lying opposite to first air inlet channel end 22.

Air outlet channel 13 has a first air outlet channel end 24, pointing toward fragrance container 14, and a second air outlet channel end 25, lying opposite to first air outlet channel end 24.

A first air inlet channel opening 26 is located in the area of first air inlet channel end 22. A first air outlet channel opening 27 is disposed in the area of first air outlet channel end 24.

A second air inlet channel opening 28 is located in the area of second air inlet channel end 23 arranged between inner tube connection 8 and outer tube connection 7. A second air outlet channel opening 29 is located in the area of second air outlet channel end 25 arranged between inner tube connection 8 and outer tube connection 7.

Second air inlet channel opening 28 and second air outlet channel opening 29 can be connected fluidically, for example, by a fluid channel or tube arrangement (not shown) of a heating, ventilation, and air conditioning system.

First air inlet channel opening 26 and first air outlet channel opening 27 are located in fragrance container 14. If a fluid, for example, air from a fresh air duct, is introduced into second air inlet channel opening 28, the fluid flows through air inlet channel 12 and first air inlet channel opening 26 into fragrance container 14. There the fluid is loaded with the fragrance located in fragrance container 14 and flows through first air outlet channel opening 27 into air outlet channel 13 and from there through second air outlet channel opening 29, for example, via a tube (not shown) into a fluid channel, which conveys the fluid augmented with the fragrance further into a vehicle cabin.

Inner tube connection 8 has an operating element 9 located centrally and perpendicular to a plane formed by its cross section. Operating element 9 is arranged sliding axially in a guide sleeve 10.

Operating element 9 has a first operating element 30, pointing toward fragrance container 14, and a second operating element 31, pointing away from fragrance container 14. In the area of second operating element end 31, operating element 9 has a circumferential first annular groove 32, which will be discussed in greater detail hereafter.

In the area of first operating element end 30, operation element 9 is coupled to a valve element 33 for motion transmission. Valve element 33 has a first valve element end 34, pointing toward fragrance container 14, and a second valve element end 35, pointing away from fragrance container 14.

In the area of first valve element end 35, valve element 33 is pretensioned, for example, against two first return springs 36, whereby the at least two first return springs 36 load valve element 33 within guide sleeve 10 in a first axial direction 37 against guide sleeve 10 and first container cover side 3. The two first return springs 36 are supported on a counter support 38, which is formed in the area of a bridge element 39. Bridge element 39 is disposed perpendicular to the longitudinal axis of air inlet channel 12 and is secured, for example, with two screws 40 to first container cover side 3.

A third annular groove 41 is situated on valve element 33 in the area of second valve element end 35. A second O-ring 42 is disposed in the area of third annular groove 41. The $2^{nd}$ O-ring lies sealingly sliding on a sleeve inner wall 43 of guide sleeve 10.

Figure 3:
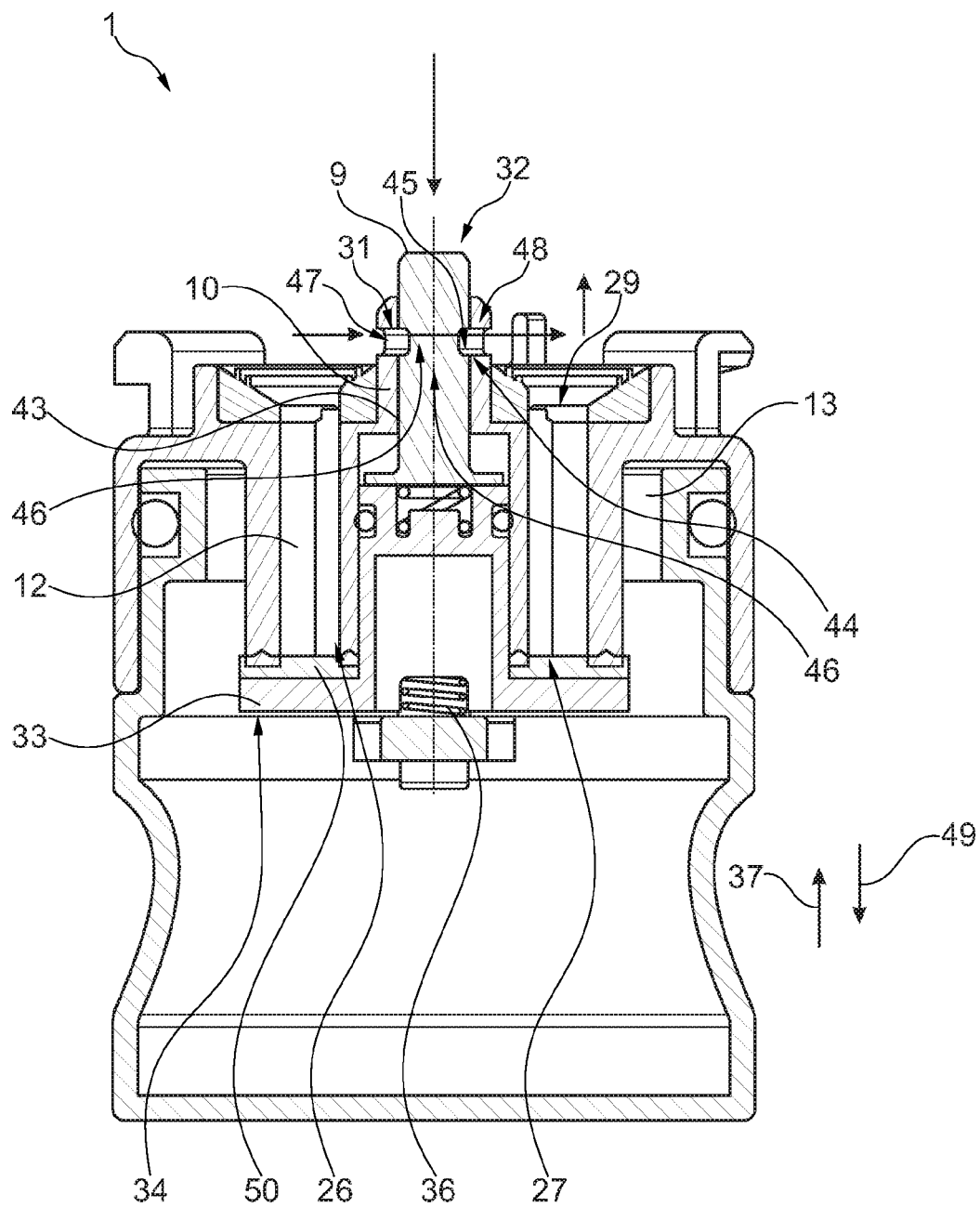
FIG. 3 shows a further side sectional view of a fragrance dispenser according to FIG. 1.

A further side sectional view of fragrance dispenser 1 is shown in FIG. 3. Operating element 9 is placed in a first operating position by means of an axial movement made relative to sleeve inner wall 43 of guide sleeve 10. First annular groove 32, situated in the area of second operating element end 31, functions here as a first bypass channel element 44, which forms a bypass channel 46 with a second bypass channel element 45 formed on guide sleeve 10. In this case, a first radial bypass inlet opening 47, located on guide sleeve 10, and a bypass outlet opening 48, formed radially on guide sleeve 10, lie sealingly against first annular groove 32.

As an example, tubes (not shown), which supply a fluid stream to bypass inlet opening 47, can be attached in the area of bypass inlet opening 47 and bypass outlet opening 48. In this case, this can be in particular a fluid stream which has been branched off from a fluid stream supplied to air inlet channel 12.

The fluid stream flows through bypass inlet opening 47 and through first annular groove 32 to bypass outlet opening 48 and from bypass outlet opening 48, for example, via a tube (not shown) into a fluid channel, which conveys the fluid into a vehicle cabin. In this case, fluid present in air outlet channel 13 is sucked out through second air outlet channel opening 29 and air outlet channel 13 is flushed in this manner.

The flow direction of the fluid stream flowing through bypass channel 46 is shown by arrows in FIG. 3.

Operating element 9 in this case can be actuated in a manner that it is movable axially in first direction 37 or in a second direction 49 opposite to first direction 37. Operating element 9 can be brought into a holding position from the first operating position in first direction 37 by an axial movement of operating element 9. In this case, first annular groove 32 is shifted axially relative to sleeve inner wall 43 and positioned arranged in first direction 37 behind bypass inlet opening 47 and bypass outlet opening 48. As a result, bypass channel 46 is closed or blocked for throughflow with a fluid.

A valve element 33 is disposed axially behind operating element 9 in second direction 49. Valve element 33 has a valve disc 50 in the area of its first valve element end 34. In the first operating position, first return springs 36 press valve disc 50 against first container cover side 3. Valve disc 50 in so doing closes first air inlet channel opening 26 and first air outlet channel opening 27 for throughflow with a fluid.

Operating element 9 can be placed in a second operating position by an axial movement of operating element 9 from the first operating position in second direction 49. In this case, first annular groove 32 is shifted relative to sleeve inner wall 43 axially in second direction 49 and positioned arranged in second direction 49 behind bypass inlet opening 47 and bypass outlet opening 48. As a result, bypass channel 46 is closed or blocked for throughflow with a fluid.

Figure 4:
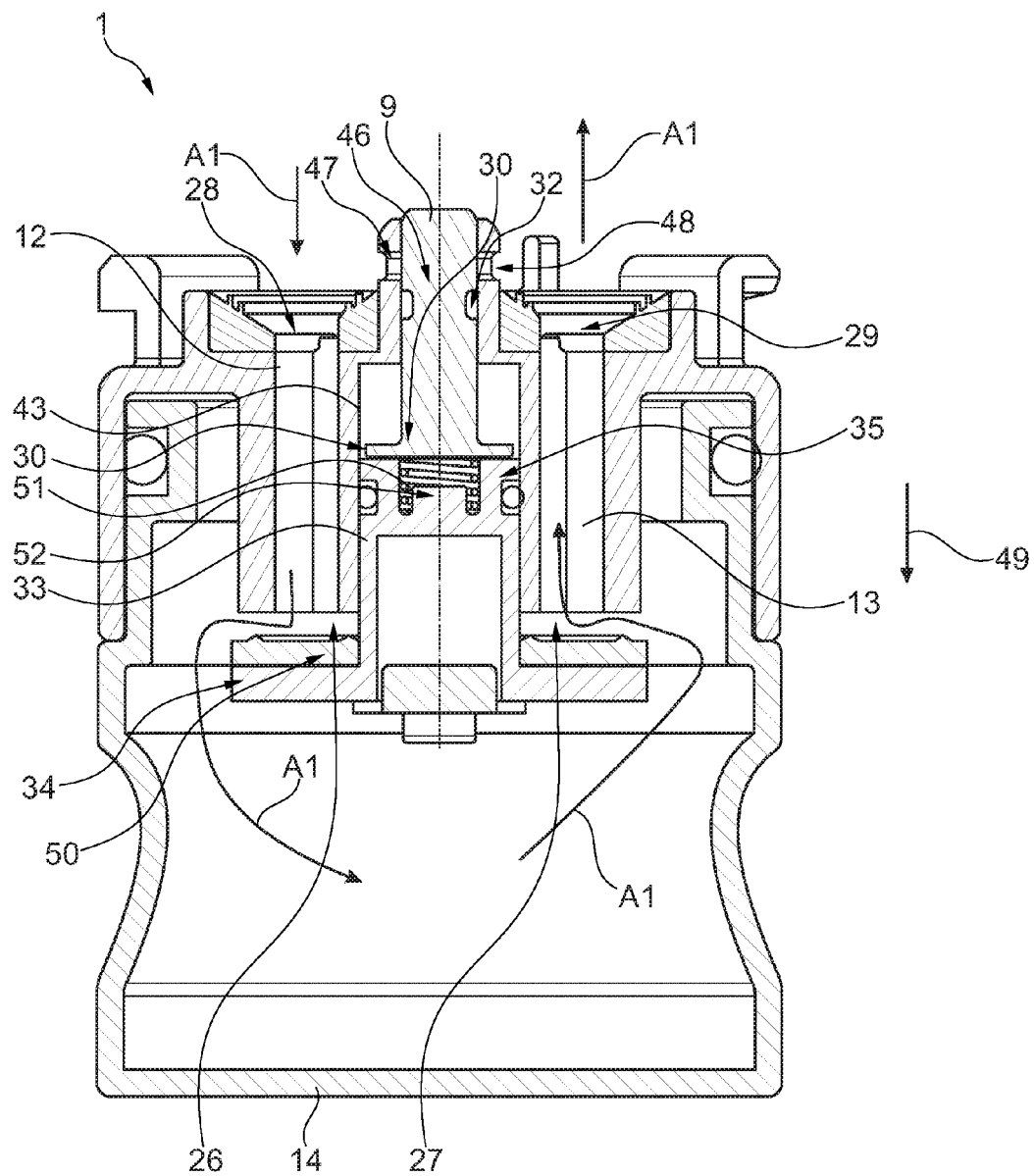
FIG. 4 shows a further side sectional view of a fragrance dispenser according to FIG. 1.

Operating element 9 disposed in fragrance dispenser 1 is shown placed in the second operating position in FIG. 4. Operating element 9 in this case compresses a second return spring 51, which is disposed or tensioned axially between first operating element end 30 and second valve element end 35. Second return spring 51 is supported against second counter support 52 formed in the area of second valve element end 35. Operating element 9 is coupled thereby to valve element 33 for a motion transmission and presses valve element 33 and a valve disc 50, located in the area of first valve element end 34, axially in second direction 49. Valve disc 50 in this case lifts itself off first air inlet channel opening 26 and first air outlet channel opening 27 and opens these for throughflow with a fluid. A fluid shown by the arrow labeled A1 in this case flows through second air inlet channel opening 28, through air inlet channel 12, and through first air inlet channel opening 26 into fragrance container 14. There the fluid is loaded with a fragrance, located in fragrance container 14, and flows through first air outlet channel opening 27, through air outlet channel 13, and second air outlet channel opening 29. The fluid is conveyed via tube attachments or fluid channel attachments (not shown) from second air outlet channel opening 29, for example, further into a vehicle cabin.

In the second operating position shown in FIG. 4, first annular groove 32 is shifted by an axial movement of operating element 9 axially relative to sleeve inner wall 43 and is positioned arranged in second direction 49 behind bypass inlet opening 47 and bypass outlet opening 48. As a result, bypass channel 46 is closed or blocked for throughflow with a fluid.

Figure 5:
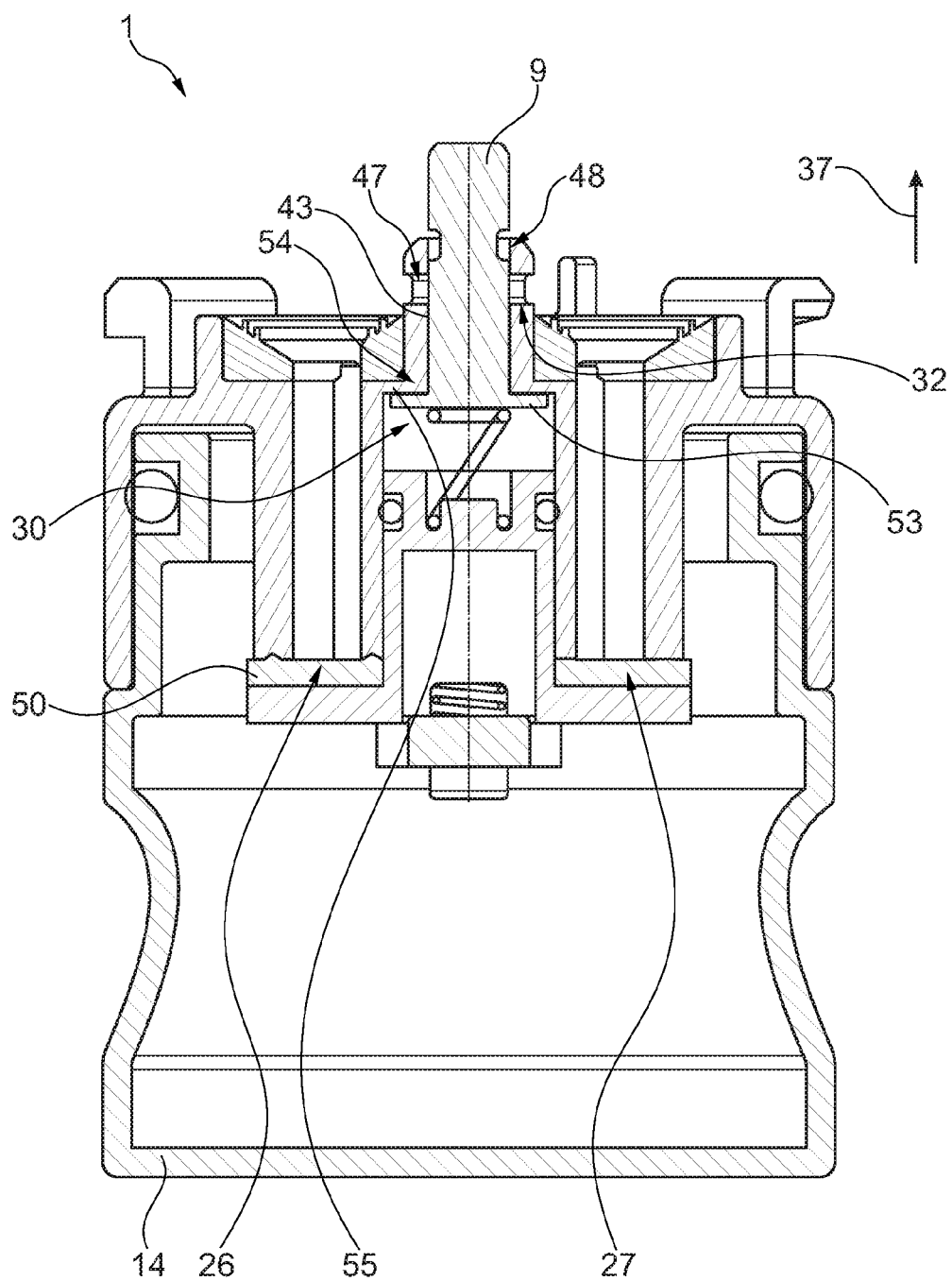
FIG. 5 shows a further side sectional view of a fragrance dispenser according to FIG. 1.

In FIG. 5 fragrance dispenser 1 is shown with an operating element 9 placed in the first operating position. Operating element 9 is moved axially so far in first direction 37 that first annular groove 32 is shifted axially relative to sleeve inner wall 43 and is positioned arranged in first direction 37 behind bypass inlet opening 47 and bypass outlet opening 48. A circumferential projection 53 is formed on first operating element end 30. Circumferential projection 53 is supported in first direction 37 against a shoulder 55 formed in the area of a first guide sleeve end 54. Valve disc 50 closes first air inlet channel opening 26 and first air outlet channel opening 27. In this case, the fluid stream through fragrance container 14 is interrupted.

Figure 6:
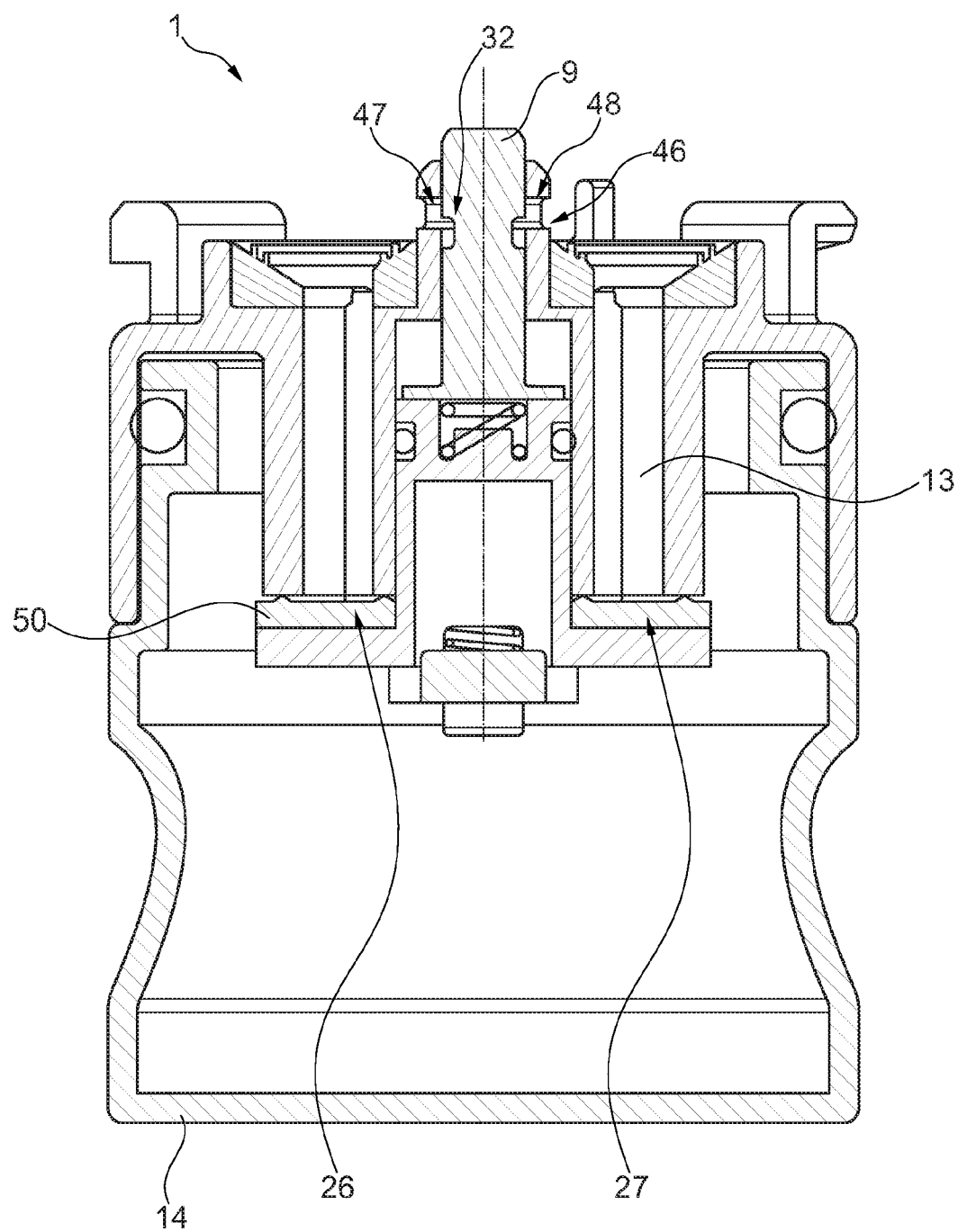
FIG. 6 shows a further side sectional view of a fragrance dispenser according to FIG. 1.

Fragrance dispenser 1 with an operating element 9 placed in a transition position between the first operating position and the second operating position is shown in FIG. 6. Bypass inlet opening 47, bypass outlet opening 48, and first annular groove 32 form a bypass channel 46 with a diameter that is greatly reduced in comparison with the first operating position. Valve disc 50 is lifted minimally from first air inlet channel opening 26 and first air outlet channel opening 27. A fluid volume that is restricted in comparison with the second operating position flows through first air inlet channel opening 26 into fragrance container 14 and from there through first air outlet channel opening 27 into air outlet channel 13. Simultaneously a fluid volume that is restricted in comparison with the first operating position flows through bypass channel 46.

Figure 7:
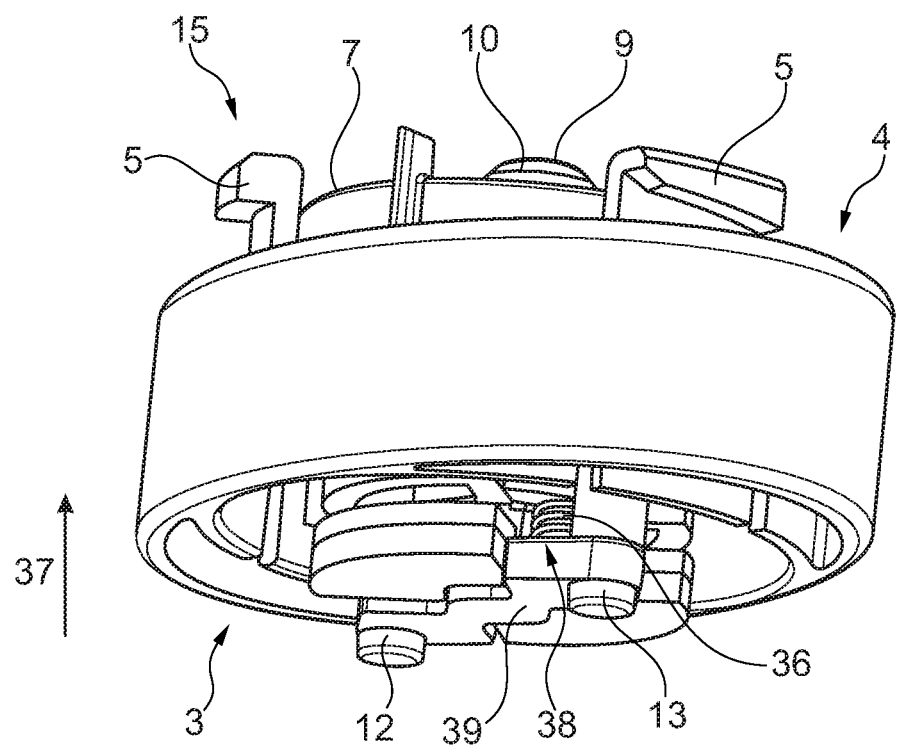
FIG. 7 shows a perspective sectional view of a container cover as part of a fragrance dispenser according to FIG. 1.

A perspective side view of container cover 15 is shown in FIG. 7. Bridge element 39 is attached to container cover 15 in the area of first container cover side 3. Bridge element 39 serves as a counter support 38 for the two first return springs 36, which load valve element 33, which is not shown in FIG. 7, in first axial direction 37 against operating element 9.

Air inlet channel 12 and air outlet channel 13 pass through bridge element 39 in a perpendicular manner.

Operating element 9 and guide sleeve 10 are disposed centrally in the area of second container cover side 4. A number of first attachment elements 5 are disposed radially outside from an outer tube connection 7; these can be connected with a number of second attachment elements, disposed on a housing element (not shown) of a heating, ventilation, and air conditioning system, to form a bayonet catch.

Figure 8:
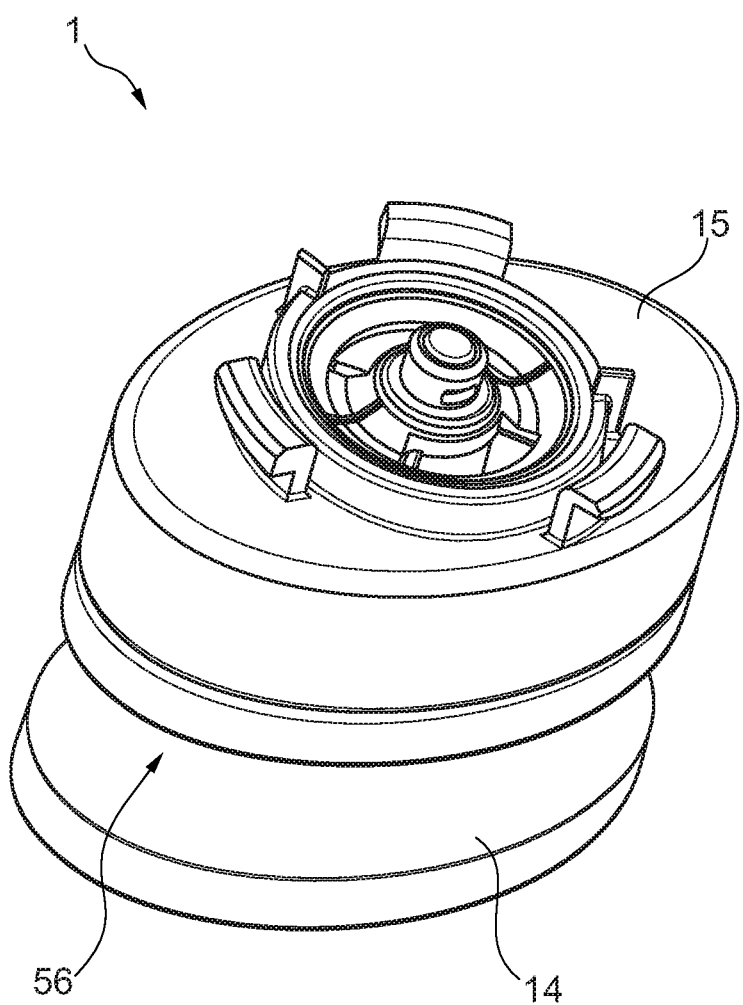
FIG. 8 shows a perspective side view of a fragrance dispenser according to FIG. 1.

A perspective side view of fragrance dispenser 1 is shown in FIG. 8. Fragrance container 14 connected to container cover 15 by way of example has a circumferential cross-sectional narrowing 56, which assures a better grip of fragrance container 14.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A fragrance dispenser for a heating, ventilation, and air conditioning system, the fragrance dispenser comprising:
   a fragrance container with a connection opening;
   a container cover with an air inlet channel and an air outlet channel;
   a movable operating element;

a movable valve element via which the air inlet channel and the air outlet channel is opened and closed, the valve element being adapted to be actuated by the operating element; and a bypass channel adapted to be controlled by the movable operating element.

2. The fragrance dispenser according to claim 1, wherein the operating element and the valve element are arranged axially one behind the other and axially slidable at least partially in a guide sleeve, and wherein the air inlet channel and the air outlet channel are arranged adjacent and substantially parallel to a longitudinal axis of the guide sleeve.

3. The fragrance dispenser according to claim 1, wherein the bypass channel has a first bypass channel element and a second bypass channel element, wherein the first bypass channel element is formed on the operating element and the second bypass channel element is formed on the guide sleeve.

4. The fragrance dispenser according to claim 3, wherein the bypass channel is opened or closed for fluid throughflow via an axial movement of the operating element made relative to the guide sleeve.

5. The fragrance dispenser according to claim 3, wherein the first bypass channel element has a circumferential first annular groove situated on the operating element and the second bypass channel element has at least one bypass inlet opening arranged radially on the guide sleeve and at least one bypass outlet opening arranged radially on the guide sleeve.

6. The fragrance dispenser according to claim 3, wherein the first bypass element has a channel passing through the operating element substantially perpendicular to the longitudinal axis of the operating element.

7. The fragrance dispenser according to claim 1, wherein the air inlet channel has a first air inlet channel opening at a first air inlet channel end pointing toward the fragrance container, and wherein the air outlet channel has a first air outlet channel opening at a first air outlet channel end pointing toward the fragrance container, and wherein the valve element has a valve disc at a first valve element end pointing toward the fragrance container, and wherein via an axial movement of the valve element and the valve disc, the first air inlet channel opening and the first air outlet channel opening are opened or closed for throughflow of a fluid.

8. The fragrance dispenser according to claim 1, wherein the valve element is loaded by at least one first return spring in a first direction pointing away from the fragrance container toward a first operating element end pointing toward the fragrance container.

9. The fragrance dispenser according to claim 1, wherein the at least one first return spring is supported against a bridge element, and wherein the bridge element is connected to a first container cover side pointing toward the fragrance container.

10. The fragrance dispenser according to claim 1, wherein the operating element is loaded by a second return spring in the first direction toward a first guide sleeve end.

11. The fragrance dispenser according to claim 1, wherein the second return spring is supported against a counter support formed in the area of a second valve element end pointing toward the operating element.

12. The fragrance dispenser according to claim 1, wherein a circumferential projection is formed at the first operating element end, wherein the circumferential projection is supported against a shoulder formed in the area of the first guide sleeve end.

13. The fragrance dispenser according to claim 1, wherein the container cover has connectors via which the air inlet channel and/or the air outlet channel and/or the bypass inlet opening and/or the bypass outlet opening are attachable to a fluid channel arrangement and/or a tube arrangement of a heating, ventilation, and air conditioning system.

14. The fragrance dispenser according to claim 1, wherein the fragrance container has an edge pointing toward the container cover, wherein at least one radially arranged circumferential second annular groove is formed on the edge, wherein at least one first O-ring, which lies against a cover inner wall formed by the container cover in a radially inwardly sealing manner is disposed in an area of the at least one second annular groove.

15. The fragrance dispenser according to claim 1, wherein the valve element in the area of the second valve element end has at least one radially arranged circumferential third annular groove, wherein at least one second O-ring, which lies against a sleeve inner wall formed by the guide sleeve in a radially inwardly sealing manner, is disposed in the area of the at least one third annular groove.

16. The fragrance dispenser according to claim 1, wherein the container cover has at least one first connecting element and the fragrance container has at least one second connecting element corresponding to the first connecting element, wherein the container cover and the fragrance container are connectable together by the two connecting elements.

17. The fragrance dispenser according to claim 1, wherein the at least one first connecting element and the at least one second connecting element form a clip and/or a plug connection.

18. The fragrance dispenser according to claim 1, wherein the container cover has at least one first attachment element, which corresponds to a second attachment element disposed on a housing element of a heating, ventilation, and air conditioning system such that the first attachment element and the second attachment element are connected together.

19. The fragrance dispenser according to claim 1, wherein the first attachment element and the second attachment element are connected to form a bayonet catch.

20. The fragrance dispenser according to claim 1, wherein the container cover on a second container cover side, lying opposite to the first container cover side, has a substantially centrally disposed attachment region, and wherein the operating element and the guide sleeve are arranged centrally within the attachment region.

21. The fragrance dispenser according to claim 1, wherein the attachment region has an inner tube connection and an outer tube connection radially surrounding the inner tube connection, wherein the operating element and the guide sleeve are arranged centrally within the inner tube connection and substantially perpendicular to a plane formed by the cross section of the inner tube connection.

22. The fragrance dispenser according to claim 1, wherein the air inlet channel has a second air inlet channel end lying opposite to the first air inlet channel end, and wherein the air outlet channel has a second air outlet channel end lying opposite to the first air outlet channel end, and wherein the second air inlet channel end and the second air outlet channel end are arranged radially between the inner tube connection and the outer tube connection.

23. A heating, ventilation, and air conditioning system, wherein at least one fragrance dispenser according to claim 1 is disposed in the heating, ventilation, and air conditioning system.

24. A heating, ventilation, and air conditioning system, wherein two fragrance dispensers according to claim 1 are disposed in the heating, ventilation, and air conditioning system.

* * * * *